United States Patent [19]

Taylor

[11] Patent Number: 4,745,922
[45] Date of Patent: May 24, 1988

[54] CERVICAL HEAT TRANSFER AND IMMOBILIZATION DEVICE

[76] Inventor: Kenneth G. Taylor, 1421 Rock Springs Ct. #2, Atlanta, Ga. 30306

[21] Appl. No.: 884,913

[22] Filed: Jul. 11, 1986

[51] Int. Cl.$^4$ .............................................. A61F 7/00
[52] U.S. Cl. ........................... 128/380; 128/DIG. 23
[58] Field of Search ............... 128/379, 380, 381, 382, 128/383, 384, 385, 386, 403, 402, 399, DIG. 23, 75, 87 B

[56] References Cited

U.S. PATENT DOCUMENTS

| | | | |
|---|---|---|---|
| D. 188,302 | 6/1960 | Monfardini | 128/DIG. 23 |
| D. 248,872 | 8/1978 | Thomas | 128/DIG. 23 |
| 1,345,906 | 7/1920 | Augustine | 128/402 |
| 1,473,506 | 11/1923 | Nessler | 128/402 |
| 1,567,931 | 12/1925 | Epler | 128/DIG. 23 |
| 1,616,961 | 2/1927 | Carter | 128/402 |
| 1,910,328 | 5/1933 | Glennan | 128/402 |
| 1,927,751 | 9/1933 | Mensi | 128/403 |
| 2,288,745 | 7/1942 | Sammis | 128/403 |
| 2,477,883 | 8/1949 | Lejohn | 128/402 |
| 2,562,121 | 7/1951 | Poux | 128/402 |
| 2,919,735 | 1/1960 | Prietzsch | 128/403 |
| 3,500,014 | 3/1970 | Longo | 128/402 |
| 3,548,819 | 12/1970 | Davis et al. | 128/82.1 |
| 3,756,226 | 9/1973 | Calabrese et al. | 128/DIG. 23 |
| 3,774,617 | 11/1973 | Lisle | 128/402 |
| 3,871,381 | 3/1975 | Roslonski | 128/402 |
| 3,882,873 | 5/1975 | Arango | 128/379 |
| 3,889,684 | 6/1975 | Lebold | 128/402 |
| 3,916,911 | 11/1975 | Sauder et al. | 128/400 |
| 4,170,998 | 10/1979 | Sauder | 128/400 |
| 4,190,054 | 2/1980 | Brennan | 128/402 |
| 4,205,667 | 6/1980 | Gaylord, Jr. | 128/DIG. 23 |
| 4,397,315 | 8/1983 | Patel | 128/403 |
| 4,427,010 | 1/1984 | Marx | 128/402 |
| 4,538,597 | 9/1985 | Lerman | 128/DIG. 23 |
| 4,543,947 | 10/1985 | Blackstone | 128/DIG. 23 |

FOREIGN PATENT DOCUMENTS

| | | | |
|---|---|---|---|
| 718686 | 9/1965 | Canada | 128/380 |
| 1346990 | 11/1963 | France | 128/380 |

OTHER PUBLICATIONS

Orthopedics Appliances Atlas, p. 223, 1952.
Journal of the American Medical Association, p. 78, Mar. 16, 1963.
Newsletter of the Pope Foundation, Inc., May 1954.
Black, P., Shepard, R. H., Markowitz, R. S.: Spinal Cord Injury in the Monkey: Rate of Cord Cooling and Temperature Gradient during Local Hypothermia. *Neurosurgery* 1979, 5:583–587.
Ciolek, J. J.: Cryotherapy, Review of Physiological Effects and Clinical Application, *Cleveland Clinic Quarterly*, 52:193–201.
Collins, W. F.: A Review of Treatment of Spinal Cord Injury, *Br. J. Surg.* 1984, 71:974–975.
Ducker, T. B., Hamit, H. E.: Experimental Treatments of Acute Spinal Cord Injury, *J. Neurosurg.* 30:693–697.
Green, B. A., Kahn, T., Raimondi, A. J.: Local Hypothermia as Treatment of Experimentally Induced Spinal Cord Contusion: Quantitative Analysis of Beneficent Effect, *Surgical Forum*, 1973, 24:436–438.
Hansebout, R. R., Kuchner, E. F., Romero-Sierra, C.: Effects of Local Hypothermia and of Steroids upon Recovery from Experimental Spinal Cord Compression Injury, *Surg. Neurol* 1975, 4:531–6.

(List continued on next page.)

*Primary Examiner*—Carl D. Friedman
*Assistant Examiner*—Michael Safavi
*Attorney, Agent, or Firm*—Kilpatrick & Cody

[57] ABSTRACT

Devices for immobilizing cervical cord injuries and applying localized temperature gradients to injured cervical cord areas. Cervical collars according to the present invention comprise a forward section and a rear section held together by fastening means such as hook and loop fasteners. The rear sections contain cavities for receiving a cooling or heating medium such as endothermic chemical packs, refrigeration coils or containers of hot or cold materials. Localized hypothermia or hyperthermia can thus be induced according to the present invention minutes or perhaps hours earlier than otherwise possible in an effort to increase the prospect of favorable prognosis for recovery of limb function.

5 Claims, 4 Drawing Sheets

OTHER PUBLICATIONS

Hansebout, R. R., Lamont, R. N., Kamath, M. V.: Effects of Local Cooling on Canine Spinal Cord Blood Flow, *Le Journal Canadien des Sciences Neurologiques*, 1985, 12:83–87.

Hansebout, R. R., Tanner, J. A., Romero-Sierra, C.: Current Status of Spinal Cord Cooling in the Treatment of Acute Spinal Cord Injury, *Spine*, 9:508–11.

Kelly, D. L., Lassiter, K. R. L., Calogero, J. A., Alexander, E.: Effects of Local Hypothermia and Tissue Oxygen Studies in Experimental Paraplegia, *J. Neurosurg.* 33:554–63.

Yashon, D., Vise, W. M., Dewey, R. C., Hunt, W. E.: Temperature of the Spinal Cord During Local Hypothermia in Dogs, *J. Neurosurg.* 39:742–45.

Single Page Product Circular by HealthCore, 281 Albany Street, Cambridge, Massachusetts for the Omnipak Cold/Hot Support Compress.

Romero-Sierra, C., Sierhuis, A., Hansebout, R., Lewin, M.: A New Method for Localised Spinal-Cord Cooling, *Med. and Biol. Eng.* 1974, pp. 188–193.

Wells, J. Hansebout, R. R.: Effects of Short and Long Term Delayed Local Cooling in Spinal Cord Injury, *Le Journal Canadien des Sciences Neurologique*, Aug., 1977:235.

Yashon, D., Bingham, W. G., Faddoul, E. M., Hunt, W. E.: Edema of the Spinal Cord Following Experimental Impact Trauma, *J. Neurosurg.*, 1973, 38:693–7.

Albin, M. S., White, R. J., Locke, G. E.: Treatment of Spinal Cord Trauma by Selective Hypothermic Perfusion, *Surgical Forum*, 1965, pp. 423–424.

Albin, M. S., White, R. J., Locke, G. S., Massopust, L. C., Kretchmer, H. E.: Localized Spinal Cord Hypothermia, *Anesthesia and Analgesia*, 1967, 46:8–16.

Albin, M. S., White, R. J., Acosta-Rua, G., Yashon, D.: Study of Functional Recovery Produced by Delayed Localized Cooling After Spinal Cord Injury in Primates, *J. Neurosurg.*, 1968, 29:113–120.

CERVICAL HEAT TRANSFER AND IMMOBILIZATION DEVICE

This invention relates to treatment of cervical cord trauma by immobilizing the cervical area and inducing localized hypothermia or hyperthermia in that area. Devices made and used according to the invention are particularly useful at the scenes of accidents and during patient extrication, and they can also be useful during other stages of treatment.

BACKGROUND OF THE INVENTION

Patients who have experienced spinal cord trauma often face a poor prognosis for full recovery. Although minor spinal cord trauma may allow a patient full return of limb function spontaneously after cord concussion, in many cases patients retain some limb function immediately after injury only to lose this function irretrievably after a few hours.

A popular theory explaining this phenomenon is that impact injury results in spinal cord swelling which may progressively enlarge the cord so that it fills the subdural and subarachnoid spaces and produces ischemic cord transection due to vascular compromise. Earlier treatment techniques, such as surgical decompression, were developed according to this theory. More recently, others have theorized that spinal cord edema following trauma causes tissue hypoxia because of impaired oxygen diffusion or compromised circulation. Some have theorized that structural alterations and possibly other factors may be more important than edema in causing the progressive neurological deterioration which sometimes accompanies spinal cord trauma. C. Romero-Sierra et al., *A New Method for Localized Spinal Cord Cooling,* Medical and Biological Engineering 188 (March 1974).

Whatever the explanation for this progressive limb function loss after spinal cord trauma, it is generally known that hypothermia reduces ischemic damage to nervous tissue. Although generalized hypothermia can induce cardiac arrest, some investigators have selectively cooled portions of the spinal cord in localized areas with success. Not only has such localized hypothermia been cited as decreasing edema and improving blood perfusion in the traumatized area, but it also is believed to decrease metabolic demands of the cooled tissue.

Previous investigation shows an improvement in recovery of experimental animals whose spinal cord impact injuries are treated with induced, local hypothermia. Such procedures have also been used on human patients with apparently promising results. R. Hansebout, *Current Status of Spinal Cord Cooling in the Treatment of Acute Spinal Cord Injury,* 9 Spine 5:508-11 (1984). It is generally agreed, however, that induced hypothermia should be initiated within at least four hours of injury, and that the earlier the cooling is started, the better the prognosis. Id., M. Albin et al., *Localized Spinal Cord Hypothermia—Anesthetic Effects and Application to Spinal Cord Injury,* 46 Anesthesiology & Analgesia 8 (1967); M. Albin, et al., *Study of Functional Recovery Produced by Delayed Localized Cooling After Spinal Cord Injury in Primates,* 29 Journal of Neurosurgery 113 (1968); B. Green et al., *Local Hypothermia as Treatment of Experimentally Induced Spinal Card Contusion: Quantitative Analysis of Beneficial Effect,* 24 Surgery Forum 436 (1973).

Investigators using 5° C. (41° F.) baths have recorded low cord temperatures of 6.7° C. (44° F.) in monkeys and a 5.4°-23.5° C. (42°-74° F.) gradient in dogs, so that subfreezing temperatures are not required for effective treatment. P. Black, *Spinal Cord Injury in the Monkey: Rate of Cord Cooling and Temperature Gradient During Local Hypothermia,* 5 Neurosurgery 583 (1979); D. Yashon, *Edema of the Spinal Cord Following Experimental Impact Trauma,* 38 Journal of Neurosurgery 693 (1973).

Experiments have also established that cooling tends to be localized, coextensive with the heat exchanger and very rapid (2-3 minutes) with extradural heat exchangers. Additionally, no significant lowering of body temperature or systemic blood pressure was encountered. C. Romero-Sierra et al., *A New Method for Localized Spinal Cord Cooling,* Medical and Biological Engineering 188 (March 1974).

Orthopedic cervical immobilization devices are currently used to extricate accident victims who experience cervical trauma and to immobilize patients' neck areas after spinal injury. U.S. Pat. No. 4,205,667 issued June 3, 1980 to Gaylord, Jr. discloses such a collar, for instance. That patent is incorporated herein by reference. The Gaylord collar comprises a pair of U-shaped body members made of air permeable foam that are sufficiently firm to provide adequate support for the wearer's head and neck. The body members are held together in a face-to-face mating arrangement with hook and loop straps.

A more widely-used collar, the Philadelphia collar, is the subject matter of U.S. Pat. No. 3,756,226 issued Sept. 4, 1973 to Calabrese et al., which is incorporated herein by reference. The Calabrese collar has two halves formed of a soft flexible polymeric material. A rigid chin support is attached to the front half while a posterior support member extends along the spine from the back of the basal portion of the skull on the other half. The halves are held together by hook and loop fabric.

Such collars may quickly be applied to a patient's neck in an effort to immobilize the cervical cord and they are typically deployed aboard emergency medical vehicles for this purpose. They do not, however, allow the doctor or medical technician to treat the cervical cord injury at the accident scene or during extrication by heating or chilling the local injury area.

SUMMARY OF THE INVENTION

Collars according to the present invention are designed not only to immobilize the cervical cord, but also to apply a localized termperature gradient to the cervical cord area. Local hypothermia can thus be induced according to the present invention minutes or perhaps hours earlier than it otherwise could have been, thereby perhaps significantly increasing prospects of favorable prognosis of patients for recovery of limb function. Such collars may be adapted to accommodate several varieties of heating and cooling means for inducing varying temperature gradients and to suit the convenience of those using the collars. For instance, endothermic chemical cooling packs are convenient and require no prior refrigeration aboard an emergency medical vehicle. On the other hand, more sophisticated vehicles may be equipped with customized refrigeration plants or pumps which can be connected to coils within these collars to cool or heat localized portions of patients' necks.

It is therefore an object of the present invention to allow a temperature gradient to be induced in the area of a patient's cervical cord injury sooner than previously feasible in order to improve the patient's prognosis for recovery of limb, motor and nerve function.

It is an additional object of the present invention to provide an inexpensive means in order to improve the quality of treatment to those who have suffered spinal cord injuries.

It is an additional object of the present invention to provide a cervical collar which not only immobilizes the cervical area during extrication of the patient from an accident, but also induces local hypothermia in the area of the injury.

It is an additional object of the present invention to provide a cervical collar similar in nature to those presently used in the field, and thus acceptable to the medical community, but which also allows for induction of localized hypothermia in the cervical area for improved treatment.

Other objects, features and advantages of the present invention will become apparent with reference to the remainder of the specification, claims and drawings.

DETAILED DESCRIPTION OF THE DRAWINGS

DETAILED DESCRIPTION OF THE DRAWINGS

Figure 1:
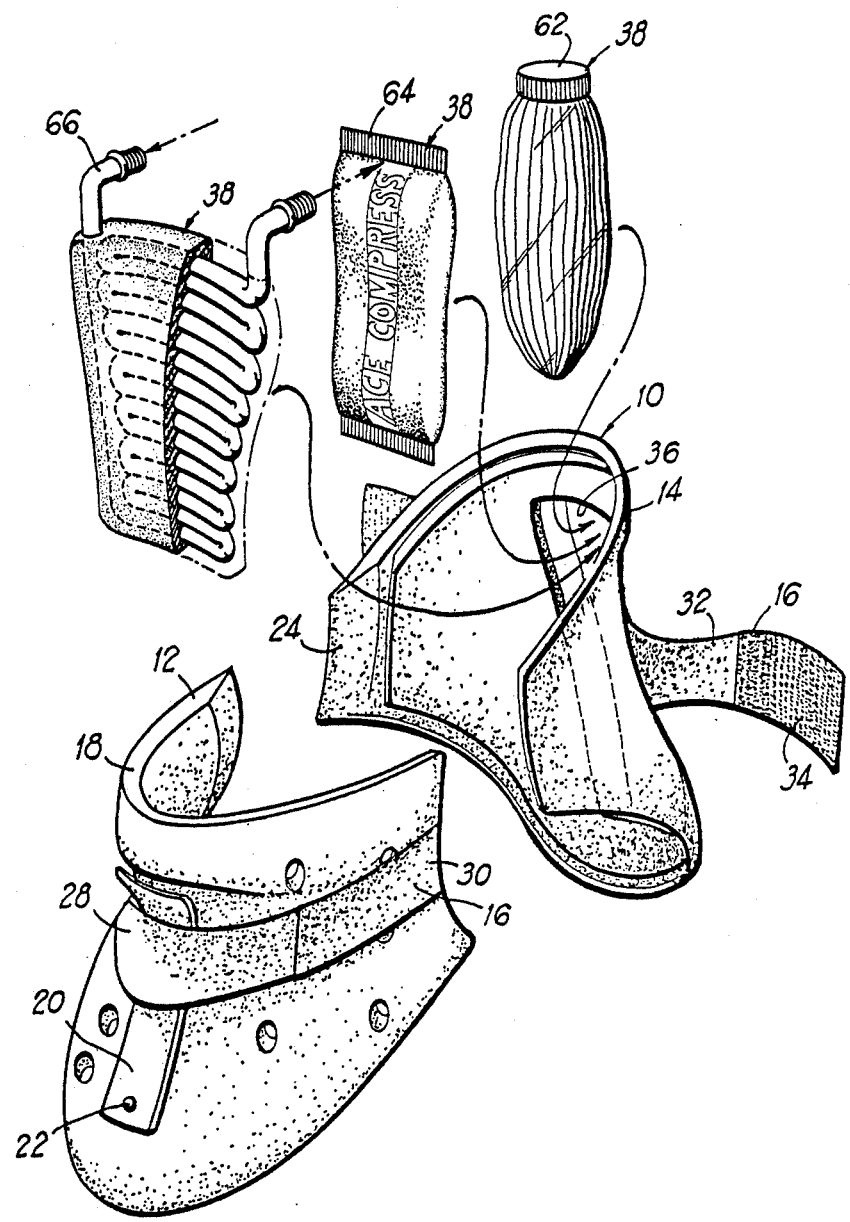
FIG. 1 is a partially exploded perspective view of a first embodiment of a collar according to the present invention.

FIG. 1 illustrates a first embodiment of a cervical collar 10 according to the present invention. Front section 12 and back section 14 of collar 10 are generally U-shaped to conform to and accommodate the front and back, respectively, of a person's neck. A connection means 16 fastens the two sections together in overlapping relationship to support the wearer's head and neck in order to immobilize the cervical area.

Front section 12 and back section 14 may be formed of any desirable material to accomplish this purpose. Generally, however, they should be formed of flexible materials to maximize the comfort of the wearer and minimize point pressures placed on his or her chin, occipital area, neck and shoulders. Rigid portions should also be included to reinforce the flexible portions and to support the wearer's head and neck. In the embodiment shown in FIG. 1, front section 12 comprises a flexible portion 18 of closed cell polymeric foam that is molded to conform to a person's chin, front neck and front shoulder areas. A rigid portion 20, which may be formed of rigid polymeric plastic materials such as rigid polystyrene, aluminum, leather or inflatable members which may be pressurized to become rigid, is attached to flexible portion 18. Suitable fasteners, such as rivets, adhesives, nuts and bolts or heat bonding may be used. Rivets 22 are used in the embodiment shown in FIG. 1 because they allow a sturdy, durable construction and a simple, inexpensive and efficient manufacturing process.

The back portion similarly comprises a flexible portion 24 and a rigid portion 26.

Figure 6:
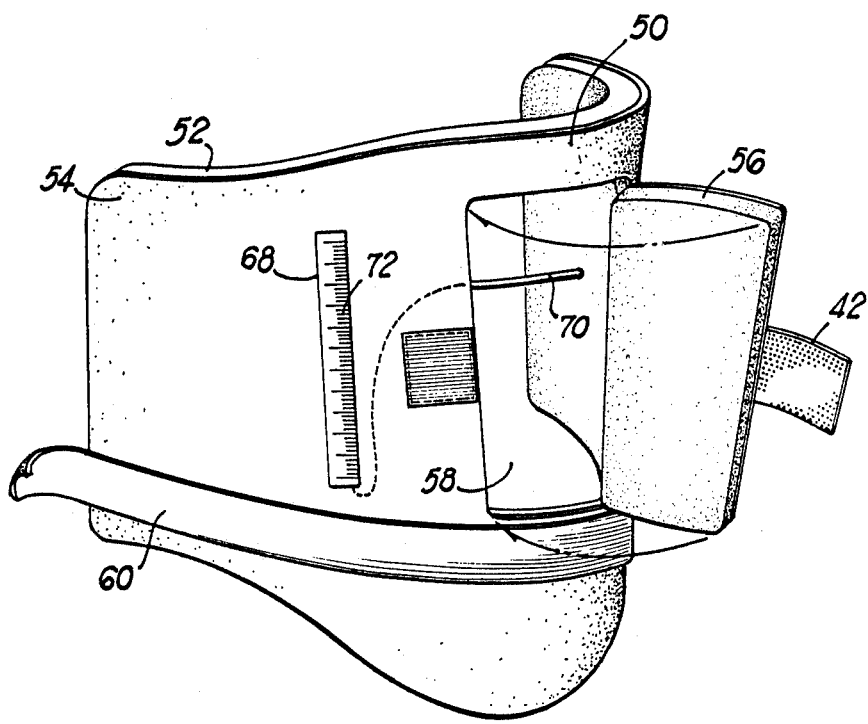
FIG. 6 is a perspective veiw of a third embodiment of a collar according to the present invention.

Other structures for front and back sections 12 and 14 may be appropriate. For instance, flexible portions 18 and 24 may comprise open cell flexible foams which are bonded to rigid external shells formed of polymeric or other appropriate material as shown in FIG. 6.

Front and back sections 12 and 14 are held together by connection means 16. Connection means 16 in the embodiment shown in FIG. 1 comprises a front strap 28 which is attached to front section 12 and rigid portion 20 and which contains hook and loop fastener sections 30. Back section 14 similarly includes a back strap 32 which contains hook and loop fastener sections 34 that cooperate with fastener sections 30 in a gripping relationship. Collar 10 may thus be applied quickly and easily and accommodated to a particular size by fitting front and back sections 12 and 14 together in an appropriate relationship and then fastening front strap 28 to back strap 32.

Figure 3:
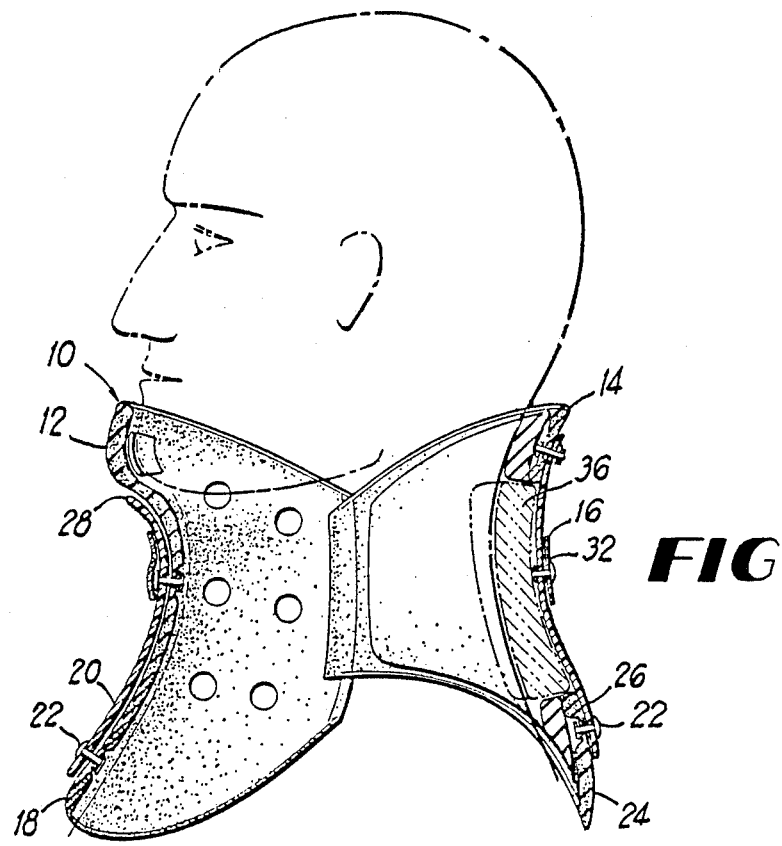
FIG. 3 is a side partial cross-sectional view of the collar of FIG. 1 applied to the patient's neck.
Figure 2:
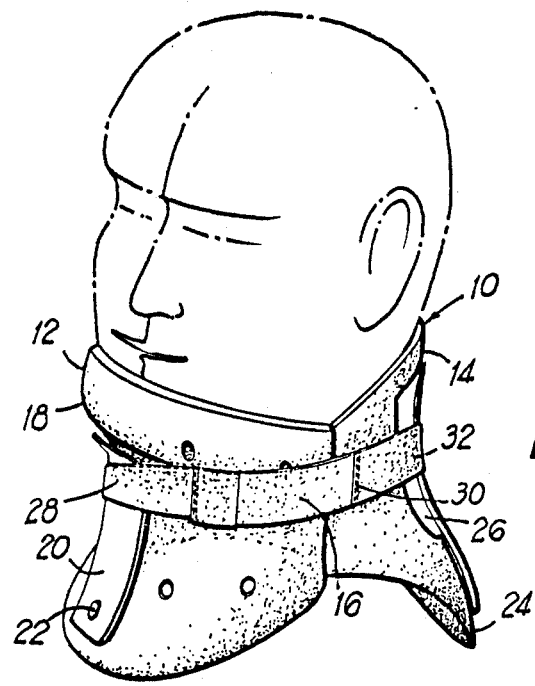
FIG. 2 is a perspective view of the collar of FIG. 1 applied to the patient's neck.
Figure 4:
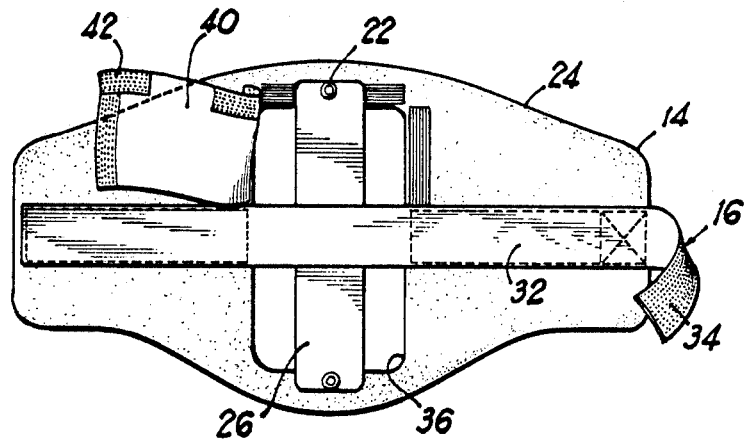
FIG. 4 is a rear plan view of the collar of FIG. 1.

Back section 14 includes a cavity 36 as shown in perspective in FIG. 1 and cross-section in FIG. 3 for containing a heat transfer means 38. Cavity 36 is preferably located below the back rigid portion 26 so that back rigid portion 26 forces heat transfer means 38 against wearer's skin and thus directly against the cervical cord area.

Where replaceable heat transfer means 38 are used, cavity 36 should be accessible from the exterior of collar 10 while worn to immobilize the neck continuously while heat transfer means 38 is being replaced. Permanent heat transfer means 38 such as refrigeration coils or conduits for carrying chilled material as discussed below, which need not be replaced or accessed while the collar 10 is being worn, do not require cavity 36 to be accessible from the exterior of collar 10; accordingly, no hatches or doors such as hatches 40 or 56 shown in FIGS. 4 and 6, respectively, are required in such cases. Cavity 36 of collar 10 shown in FIG. 4 accomplishes this purpose by providing an access hatch 40 located to one side of rigid portion 26 and above back strap 32. Hatch 40 may be located conveniently on either side of rigid portion 26 and above and below strap 32 and oriented to open in any desired direction. A suitable fastener such as hook and loop tab 42 may be utilized to hold hatch 40 in place. Hatch 40 is not necessary; back section 14 may simply include an opening communicating with cavity 36 through which heat transfer means 38 may be inserted. Hatch 40 does, however, add insulation to maintain desired temperature on the wearer's necks, and it adds strength to back section 14.

Figure 5:
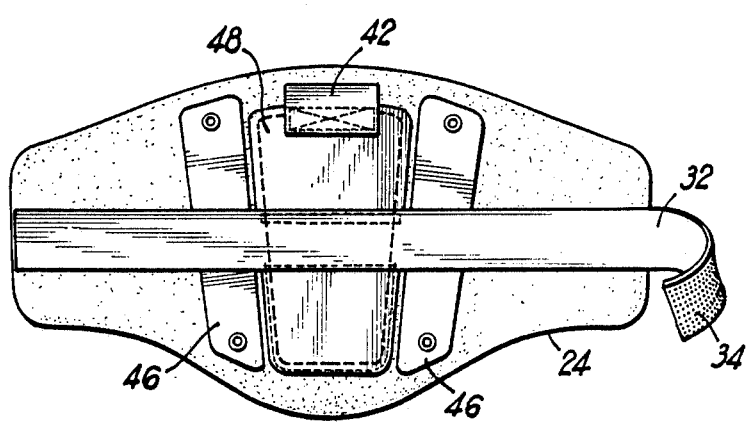
FIG. 5 is a rear plan view of a second embodiment of a collar according to the present invention.

A second embodiment of collar 10 is partially shown in FIG. 5, which illustrates a rear plan view of back section 14. Back section 44 includes two rigid portions 46 which are located to either side of the center of back section 44. An access hatch 48 is located between rigid portions 46 to accept heat transfer means 38. Back section 44 of this second embodiment places less direct pressure on heat transfer means 38 and therefore on the wearer's cervical cord.

FIG. 6 illustrates a third embodiment in which back section 50 (and the corresponding front section) are formed of foam flexible portions 52 and rigid portions 54 are a hard shell of polymeric material bonded or adhered to flexible portions 52. Hatch 56 in this embodiment may be centered on back section 50 and direct pressure applied by rigid portions 54 to the wearer's cervical cord. Heat transfer means 38 may conveniently be inserted straight down into cavity 58 with no need to squeeze it diagonally between a rigid structural member and the back strap 60.

Heat transfer means 38 may take any of a number of forms. It may comprise a pouch or container 62 which can be opened and closed to receive suitable heated or chilled materials. Such materials may comprise, for instance, an ice/water bath slurry, an ice/alcohol slurry, dry ice, a combination of these materials or other appropriate materials for cooling the cervical cord. Alternatively, they may comprise hot water or other appropriate material for heating the cord.

Heat transfer means 38 may also comprise a chemical cold pack such as one of those currently commercially available. Such a cold pack may conveniently be stored without the need for refrigeration aboard an emergency medical vehicle. Typical cold packs 64 currently commercially available comprise a first compartment containing a first endothermic reagent and a second compartment containing a second endothermic reagent. The compartments are separated by a barrier which may be physicially broken to initiate the chemical reaction. Such a cold pack 64 is disclosed in U.S. Pat. No. 4,427,010 issued Jan. 24, 1984 to Marks, which patent is incorporated herein by this reference. The endothermic reagents disclosed in that patent are xylite and water or alcohol. Ammonium nitrate and water or other well known endothermic reagents may similarly be used as endothermic reagents.

A third form of heat transfer means 38 may be heat exchanger coils 66. These may be coils designed and constructed for low pressure cirrculation of chilled or heated materials or they may be coils which are connected to a refrigeration compressor for flow of compressed refrigerant. The coils may be permanently connected to refrigeration system and simply inserted into an appropriate collar 10 for use. Alternatively, coils 66 may be fitted with quick disconnect means and permanently placed in collar 10. Refrigeration systems which may be used with the present invention are disclosed in U.S. Pat. No. 4,170,998 issued Oct. 16, 1979 to Sauder, and U.S. Pat. No. 3,916,911 issued Nov. 4, 1975 to Sauder et al., which patents are incorporated herein by reference.

A thermometer 68 may also be used in connection with collar 10 as shown in FIG. 6. Thermometer 68 may have a sensor 70 located adjacent the wearer's cervical cord area and heat transfer means 38. A readout 72 may be located on the exterior of collar 10 or in another convenient location to inform the treating technician or doctor when heat transfer means 38 needs to be replaced or flow to it of chilled or heated materials increased or decreased.

Collar 10 is applied to the wearer according to conventional medical procedures followed in connection with current cervical immobilization collars. Before, during or after application, heat transfer means 38 may be inserted into collar 10, preferably as soon after injury as possible to induce cooling or heating to the injured cervical cord. Temperature of the area should be monitored and heat transfer means 38 replaced when necessary, or flow to it of heated or chilled materials increased or decreased when necessary, to ensure induction of proper temperature gradient.

This disclosure is provided for purposes of illustration and explanation. Modifications may be made to the specific embodiments disclosed without departing from the scope and spirit of the invention.

I claim:

1. A collar for immobilizing a person's neck and inducing hypothermia in the person's cervical cord and an area of the back of the person's neck above or adjacent to the cervical cord, comprising:
    (a) a front section comprising a generally U-shaped flexible portion having an exterior and an interior surface and formed of polymeric foam material; and a front rigid member attached to the exterior surface of the flexible portion to support the flexible portion and to allow the flexible portion to conform to the person's neck;
    (b) a rear section comprising a generally U-shaped flexible portion having an exterior and an interior surface and formed of polymeric foam material; a rear rigid member attached to the exterior surface of the flexible portion and oriented to be generally parallel to the person's cervical cord when the collar is worn to support the flexible portion and to allow the flexible portion to conform to the person's neck; and a cavity formed in the rear flexible portion so as to be at least partially overlain by the rear rigid member, to open on the interior surface of the rear section only over an area corresponding to said area of the back of the person's neck above or adjacent to the cervical cord, and dimensioned to correspond to said area;
    (c) a cooling medium in the cavity for inducing hypothermia in the cervical cord; and
    (d) a strap attached to the rear section so as to overlie at least a portion of the rear section cavity, which strap contains at least one section of hook and loop fastener material and which strap retains the front and rear sections together and forces the rear rigid member and the cooling medium against the person's neck to increase the hypothermic effect on the cervical cord.

2. A device according to claim 1 in which the cooling medium comprises a pouch mounted in the rear section cavity which includes a first compartment containing a first endothermic reagent, a second compartment containing a second endothermic reagent and a barrier separating the two compartments which may be physically broken to initiate an endothermic chemical reaction.

3. A device according to claim 1 in which the cooling medium comprises at least one conduit mounted in the rear section cavity, chilled material within the conduit, and means for circulating the chilled material through the conduit.

4. A device according to claim 1 in which the cooling medium comprises at least one refrigeration coil mounted in the rear section cavity, refrigerant within the coil, and refrigeration means for compressing and circulating the refrigerant within the coil.

5. A device according to claim 1 in which the cooling medium comprises a bag filled with ice mounted in the rear section cavity.

* * * * *